(12) United States Patent
Hosokawa et al.

(10) Patent No.: US 7,981,523 B2
(45) Date of Patent: Jul. 19, 2011

(54) AROMATIC AMINE DERIVATIVE AND ORGANIC ELECTROLUMINESCENCE DEVICE USING THE SAME

(75) Inventors: Chishio Hosokawa, Chiba (JP); Masahiro Kawamura, Chiba (JP); Masakazu Funahashi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 1116 days.

(21) Appl. No.: 11/378,332

(22) Filed: Mar. 20, 2006

(65) Prior Publication Data

US 2006/0251925 A1  Nov. 9, 2006

(30) Foreign Application Priority Data

Apr. 18, 2005  (JP) .................................. 2005-119880

(51) Int. Cl.
    *H01L 51/54* (2006.01)
(52) U.S. Cl. ......... 428/690; 428/917; 313/504; 313/506
(58) Field of Classification Search .................. None
    See application file for complete search history.

(56) References Cited

U.S. PATENT DOCUMENTS

| | | | |
|---|---|---|---|
| 6,280,859 B1 * | 8/2001 | Onikubo et al. | 428/690 |
| 6,743,948 B1 | 6/2004 | Hosokawa et al. | |
| 6,951,693 B2 | 10/2005 | Hosokawa et al. | |
| 2003/0072966 A1 * | 4/2003 | Hosokawa et al. | 428/690 |
| 2003/0118866 A1 * | 6/2003 | Oh et al. | 428/690 |
| 2005/0038296 A1 | 2/2005 | Hosokawa et al. | |
| 2005/0156164 A1 | 7/2005 | Sotoyama | |

FOREIGN PATENT DOCUMENTS

| | | |
|---|---|---|
| EP | 1 619 177 A1 | 1/2006 |
| JP | 6-240245 | 8/1994 |
| JP | 2002-324678 | 11/2002 |
| JP | 2003-109765 | 4/2003 |
| JP | 2004-87245 | 3/2004 |
| WO | WO 2004/096743 A1 | 11/2004 |

OTHER PUBLICATIONS

U.S. Appl. No. 11/550,519, filed Oct. 18, 2006, Funahashi, et al.
U.S. Appl. No. 11/596,299, filed Nov. 13, 2006, Funahashi.
U.S. Appl. No. 11/624,255, filed Jan. 18, 2007, Hosakawa, et al.
U.S. Appl. No. 11/575,441, filed Mar. 16, 2007, Funahashi.
U.S. Appl. No. 11/344,604, filed Feb. 1, 2006, Hosokawa, et al.
U.S. Appl. No. 11/428,969, Jul. 6, 2006, Kawamura, et al.
U.S. Appl. No. 12/854,247, filed Aug. 11, 2010, Funahashi, et al.

* cited by examiner

*Primary Examiner* — Dawn Garrett

(74) *Attorney, Agent, or Firm* — Oblon, Spivak, McClelland, Maier & Neustadt, L.L.P.

(57) ABSTRACT

To provide an organic electroluminescence device having high emission luminance, high heat resistance, excellent high-temperature storage stability, and a long lifetime, and an aromatic amine derivative for realizing the device. Provided are a novel aromatic amine derivative having a specific structure and an organic electroluminescence device including: a cathode; an anode; and one or multiple organic thin film layers including at least a light-emitting layer, the one or multiple organic thin film layers being interposed between the cathode and the anode, in which at least one layer of the one or multiple organic thin film layers contains the aromatic amine compound alone or as a component of a mixture.

13 Claims, 5 Drawing Sheets

AROMATIC AMINE DERIVATIVE AND ORGANIC ELECTROLUMINESCENCE DEVICE USING THE SAME

CROSS-REFERENCE TO RELATED APPLICATIONS

The present application claims priority to Japanese patent application JP 2005-119880, filed on Apr. 18, 2005.

TECHNICAL FIELD

The present invention relates to an aromatic amine derivative and an organic electroluminescence (EL) device using the same. More specifically, the present invention relates to an organic EL device having high emission luminance, high heat resistance, excellent high-temperature storage stability, and a long lifetime and to an aromatic amine derivative for realizing the organic EL device.

BACKGROUND ART

An organic EL device using an organic substance has been used as the flat luminous body of a wall hanging television or as a light source for, for example, the backlight of a display, and has been vigorously developed.

The electroluminescence phenomenon of an organic material was observed in an anthracene single crystal by Pope et al. in 1963 (J. Chem. Phys. 38 (1963) 2042). In 1965, Helfinch and Schneider succeeded in observing relatively strong injection-type EL by means of a solution electrode system having good injection efficiency (Phys. Rev. Lett. 14 (1965) 229). As reported since then, research has been conducted on the formation of an organic light-emitting substance by means of a conjugate organic host substance and a conjugate organic activator having a fused benzene ring. Examples of the organic host substance include naphthalene, anthracene, phenanthrene, tetracene, pyrene, benzopyrene, chrysene, picene, carbazole, fluorene, biphenyl, terphenyl, triphenylene oxide, dihalobiphenyl, trans-stilbene, and 1,4-diphenylbutadiene. Examples of the activator include anthracene, tetracene, and pentacene. However, each of those organic light-emitting substances is present in the form of a single layer having a thickness in excess of 1 μm, so a high electric field is needed to cause such substance to emit light. Therefore, research on a thin film device by means of a vacuum deposition method has been conducted (for example, Thin Solid Films 94 (1982) 171). A reduction in thickness has been effective in reducing a driving voltage, but has not attained a device having luminance high enough to be put into practical use.

In view of the foregoing, Tang et al. have devised an EL device obtained by laminating two extremely thin layers (a hole-transporting layer and a light-emitting layer) between an anode and a cathode by means of a vacuum deposition, and have realized high luminance at a low driving voltage (Non-Patent Document 1 or Patent Document 1). After that, as a result of ten and several years of development of an organic compound to be used in each of the hole-transporting layer and the light-emitting layer, a lifetime and luminous efficiency at practical levels have been achieved. As a result, an organic EL device has started to be practically used in, for example, the display portion of a car stereo or of a portable phone.

However, the organic EL device has, for example, practically insufficient emission luminous and practically insufficient durability against the deterioration of the device with time due to long-term use, so the additional improvement of the device has been requested. In particular, when one attempts to apply the device to a full-color display or the like, the device is requested to achieve a half life of several thousand hours or longer at a high luminance of 300 cd/m$^2$ or more for each of R, G, and B colors. It is difficult to achieve such half life particularly in the case of blue light emission. Blue light emission requires a large energy gap of the light-emitting layer (2.8 eV or more). In addition, an energy barrier upon hole injection between the hole-transporting layer and the light-emitting layer is large. Accordingly, the intensity of an electric field to be applied to an interface between the hole-transporting layer and the light-emitting layer is large. Therefore, the conventional hole-transporting layer has not allowed stable hole injection, so the improvement of the layer has been requested.

In addition, it has been pointed out that the storage performance of the organic EL device at a high temperature equal to or higher than 100° C. is problematic on the precondition that the device is mounted on a vehicle. At this time as well, it has been pointed out that the glass transition temperature of the conventional hole-transporting layer is low. One has attempted to increase the glass transition temperature to 100° C. or higher to cope with the problem. However, this approach has been still insufficient to realize good storage performance at a high temperature. Furthermore, there has been a problem in that an exciplex occurs as an interaction between the hole-transporting layer and the light-emitting layer to deteriorate the luminance of the device.

Patent Document 1: U.S. Pat. No. 4,356,429
Non-Patent Document 1: Appl. Phys. Lett. 51 (1987) 913

DISCLOSURE OF THE INVENTION

Problems to be Solved by the Invention

The present invention has been made with a view to solving the above problems, and an object of the present invention is to provide an organic EL device having high emission luminance, high heat resistance, and a long lifetime, and an aromatic amine derivative for realizing the device.

Means for Solving the Problems

The inventors of the present invention have made extensive studies with a view to achieving the above object. As a result, they have found that the use of an aromatic amine derivative having a diphenylaminoaryl group bound to a central pyrene skeleton as a material for an organic EL device improves the emission luminance, heat resistance, and lifetime of the device, thereby completing the present invention.

In other words, the present invention provides an aromatic amine derivative represented by the following general formula (1):

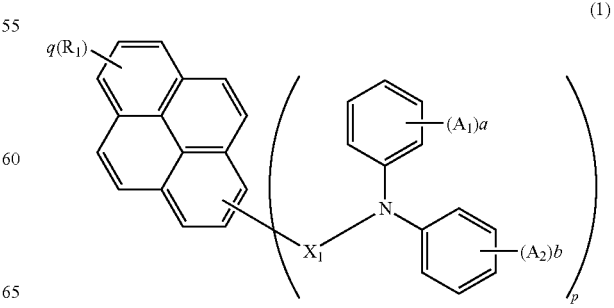

where: $A_1$, $A_2$, and $R_1$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 6 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted heterocyclic group having 5 to 50 carbon atoms, or a halogen atom, and $A_1$ and $A_2$ may bind to each other to form a saturated or unsaturated ring;

a and b each represent an integer of 0 to 5, and multiple $A_1$s and multiple $A_2$s may be identical to or different from each other, and may bind to each other to form a saturated or unsaturated ring when a and b each represent 2 or more;

p represents an integer of 1 to 4, and groups in ( ) may be identical to or different from each other when p represents 2 or more;

q represents an integer of 0 to 9, and multiple $R_1$s may be identical to or different from each other when q represents 2 or more; and $X_1$ represents a substituted or unsubstituted arylene group having 5 to 50 carbon atoms.

In addition, the present invention provides an organic EL device including: a cathode; an anode; and one or multiple organic thin film layers including at least a light-emitting layer, the one or multiple organic thin film layers being interposed between the cathode and the anode, in which at least one layer of the one or multiple organic thin film layers contains the aromatic amine derivative alone or as a component of a mixture.

Effect of the Invention

Each of the aromatic amine derivative of the present invention and the organic EL device using the derivative has high emission luminance, high heat resistance, excellent high-temperature storage stability, and a long lifetime.

BEST MODE FOR CARRYING OUT THE INVENTION

Figure 1:
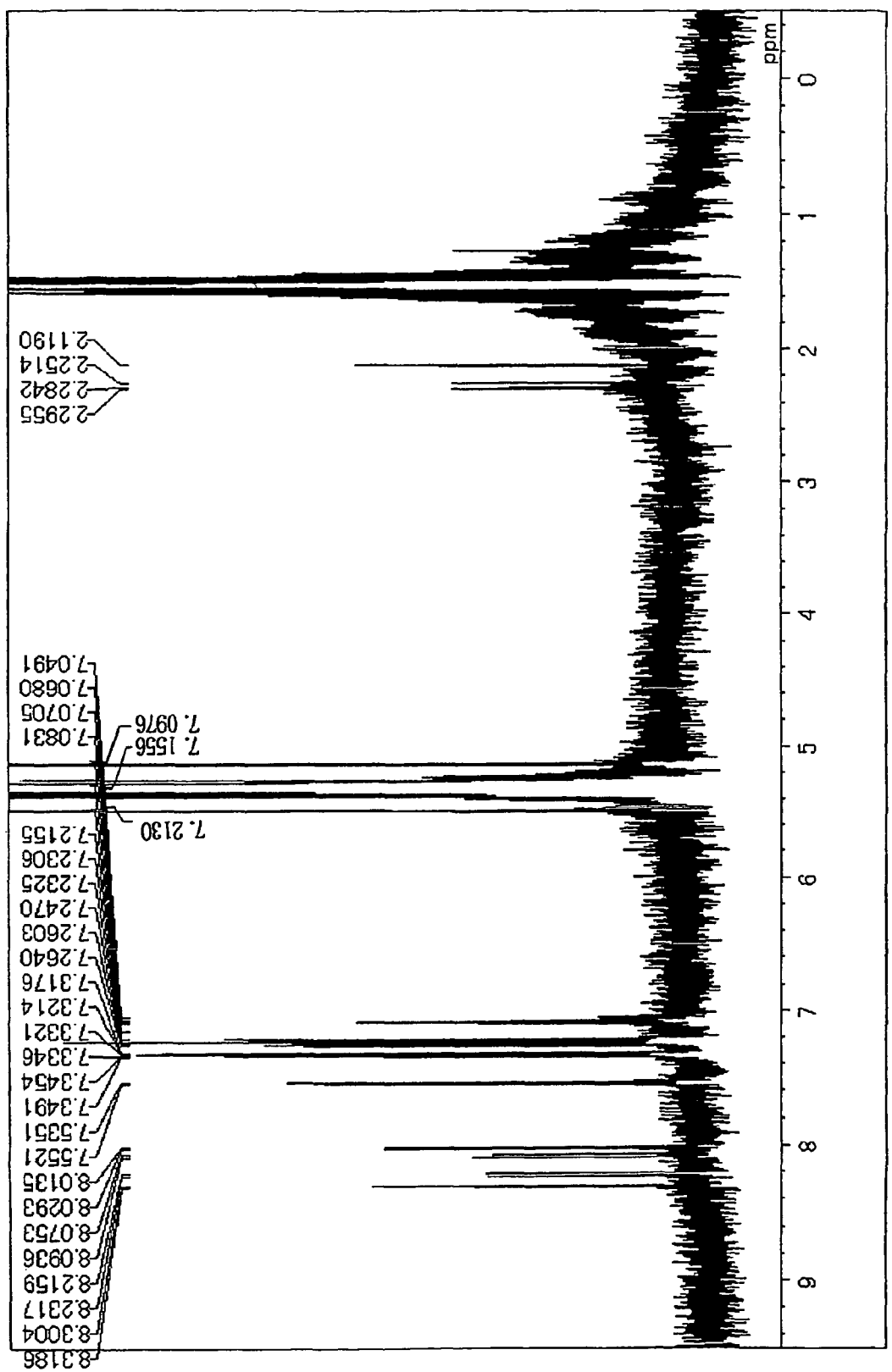
FIG. 1 A view showing the $^1$H-NMR spectrum of Compound (1) obtained in Synthesis Example 1.

Hereinafter, first, an aromatic amine derivative of the present invention represented by the following general formula (1) will be described.

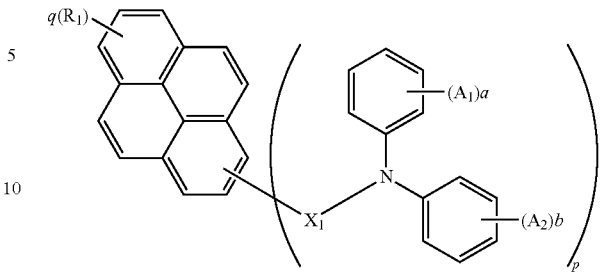

(1)

In the general formula (1): $A_1$, $A_2$, and $R_1$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 6 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted heterocyclic group having 5 to 50 carbon atoms, or a halogen atom, and $A_1$ and $A_2$ may bind to each other to form a saturated or unsaturated ring;

a and b each represent an integer of 0 to 5, preferably 0 to 3, and multiple $A_1$s and multiple $A_2$s may be identical to or different from each other, and may bind to each other to form a saturated or unsaturated ring when a and b each represent 2 or more;

p represents an integer of 1 to 4, preferably 2 to 4, and groups in ( ) may be identical to or different from each other when p represents 2 or more;

q represents an integer of 0 to 9, preferably 0 to 4, and multiple $R_1$s may be identical to or different from each other when q represents 2 or more; and $X_1$ represents a substituted or unsubstituted arylene group having 5 to 50 carbon atoms.

Examples of the alkyl group represented by each of $A_1$, $A_2$, and $R_1$ include, for example, a methyl group, an ethyl group, a propyl group, an isopropyl group, a n-butyl group, a s-butyl group, an isobutyl group, a t-butyl group, a n-pentyl group, a n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

Of those, a methyl group, an ethyl group, an n-propyl group, an isopropyl group, an n-butyl group, an s-butyl group, a t-butyl group, an n-pentyl group, and an n-hexyl group are preferable.

Examples of the aryl group represented by each of $A_1$, $A_2$, and $R_1$ include, for example, a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4''-t-butyl-p-terphenyl-4-yl group, an o-cumenyl group, a m-cumenyl group, a p-cumenyl group, a 2,3-xylylenyl group, a 3,4-xylylenyl group, a 2,5-xylylenyl group, a mesitylenyl group, a perfluorophenyl group, an anthranyl group, a phenanthryl group, a pyrenyl group, a chrysenyl group, a fluoranthenyl group, and a fluorenyl group.

Of those, a phenyl group, a naphthyl group, a biphenyl group, an anthranyl group, a phenanthryl group, a pyrenyl group, a chrysenyl group, a fluoranthenyl group, and a fluorenyl group are preferable.

Examples of the aralkyl group represented by each of $A_1$, $A_2$, and $R_1$ include, for example, a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, a m-methylbenzyl group, an o-methylbenzyl group, a p-chlorobenzyl group, a m-chlorobenzyl group, an o-chlorobenzyl group, a p-bromobenzyl group, a m-bromobenzyl group, an o-bromobenzyl group, a p-iodobenzyl group, a m-iodobenzyl group, an o-iodobenzyl group, a p-hydroxybenzyl group, a m-hydroxybenzyl group, an o-hydroxybenzyl group, a p-aminobenzyl group, a m-aminobenzyl group, an o-aminobenzyl group, a p-nitrobenzyl group, a m-nitrobenzyl group, an o-nitrobenzyl group, a p-cyanobenzyl group, a m-cyanobenzyl group, an o-cyanobenzyl group, a 1-hydroxy-2-phenylisopropyl group, and a 1-chloro-2-phenylisopropyl group.

Examples of the cycloalkyl group represented by each of $A_1$, $A_2$, and $R_1$ include, for example, a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group. A cyclopentyl group and a cyclohexyl group are preferable.

The alkoxy group represented by each of $A_1$, $A_2$, and $R_1$ is a group represented by —OY, and examples of Y include the same groups as those described with respect to the alkyl group.

The aryloxy group represented by each of $A_1$, $A_2$, and $R_1$ is a group represented by —OY', and examples of Y' include the same groups as those described with respect to the aryl group.

An example of the arylamino group represented by each of $A_1$, $A_2$, and $R_1$ includes, for example, an amino group substituted by the aryl group.

An example of the alkylamino group represented by each of $A_1$, $A_2$, and $R_1$ includes an amino group substituted by the alkyl group.

Examples of the heterocyclic group represented by each of $A_1$, $A_2$, and $R_1$ include, for example, a 1-pyrolyl group, a 2-pyrolyl group, a 3-pyrolyl group, a pyradinyl group, a 2-pyridinyl group, a 1-imidazolyl group, a 2-imidazolyl group, a 1-pyrazolyl group, a 1-indolidinyl group, a 2-indolidinyl group, a 3-indolidinyl group, a 5-indolidinyl group, a 6-indolidinyl group, a 7-indolidinyl group, an 8-indolidinyl group, a 2-imidazopyridinyl group, a 3-imidazopyridinyl group, a 5-imidazopyridinyl group, a 6-imidazopyridinyl group, a 7-imidazopyridinyl group, a 8-imidazopyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a β-carbolin-1-yl, a β-carbolin-3-yl, a β-carbolin-4-yl, a β-carbolin-5-yl, a β-carbolin-6-yl, a β-carbolin-7-yl, a β-carbolin-8-yl, a β-carbolin-9-yl, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acridinyl group, a 2-acridinyl group, a 3-acridinyl group, 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin- 1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenadinyl group, a 2-phenadinyl group, a 1-phenothiadinyl group, a 2-phenothiadinyl group, a 3-phenothiadinyl group, a 4-phenothiadinyl group, a 10-phenothiadinyl group, a 1-phenoxadinyl group, a 2-phenoxadinyl group, a 3-phenoxadinyl group, a 4-phenoxadinyl group, a 10-phenoxadinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl-3-indolyl group, a 4-t-butyl-3-indolyl group, pyrrolidine, pyrazolidine, and piperalidine.

Examples of the halogen atom represented by each of $A_1$, $A_2$, and $R_1$ include a fluorine atom, a chlorine atom, a bromine atom, and an iodine atom.

Furthermore, examples of a ring when $A_1$ and $A_2$, and multiple $A_1$'s and multiple $A_2$'s each are formed in a ring include: cycloalkanes each having 4 to 12 carbon atoms such as cyclobutane, cyclopentane, cyclohexane, adamantane, and norbornane; cycloalkenes each having 4 to 12 carbon atoms such as cyclobutene, cyclopentene, cyclohexene, cycloheptene, and cyclooctene; cycloalkadienes each having 6 to 12 carbon atoms such as cyclohexadiene, cycloheptadiene, and cyclooctadiene; aromatic rings each having 6 to 50 carbon atoms such as benzene, naphthalene, phenanthrene, anthracene, pyrene, chrysene, and acenaphthylene; and heterocyclic rings each having 5 to 50 carbon atoms such as imidazole, pyrrole, flan, thiophene, and pyridine.

Examples of the arylene group represented by $X_1$ include bivalent groups of examples listed in the aryl groups represented by each of $A_1$, $A_2$ and $R_1$. A phenylene group, a naphthylene group, a biphenylene group, an anthranylene group, a perylenylene group, and a pyrenylene group are preferable.

Furthermore, examples of a substituent of each group represented by each of $A_1$, $A_2$, $R_1$, and $X_1$ include a substituted or unsubstituted aryl group having 5 to 50 nuclear carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 nuclear carbon atoms, a substituted or unsubstituted aryloxy group having 5 to 50 nuclear carbon atoms, a substituted or unsubstituted arylthio group having 5 to 50 nuclear carbon atoms, a substituted or unsubstituted alkoxycarbonyl group having 1 to 50 carbon atoms, an amino group, a halogen atom, a cyano group, a nitro group, a hydroxyl group, and a carboxyl group.

Of those, an alkyl group having 1 to 10 carbon atoms, a cycloalkyl group having 5 to 7 carbon atoms, and an alkoxy group having 1 to 10 carbon atoms are preferable, an alkyl group having 1 to 6 carbon atoms and a cycloalkyl group having 5 to 7 carbon atoms are more preferable, and a methyl group, an ethyl group, an n-propyl group, an isopropyl group, an n-butyl group, a sec-butyl group, a tert-butyl group, an n-pentyl group, an n-hexyl group, a cyclopentyl group, and a cyclohexyl group are particularly preferable.

In addition, the aromatic amine derivative represented by the general formula (1) of the present invention is preferably of a structure represented by the following general formula (2) in which q represents 0. $A_1$, $A_2$, $X_1$, a, b, and p each have the same meaning as that of the general formula (1).

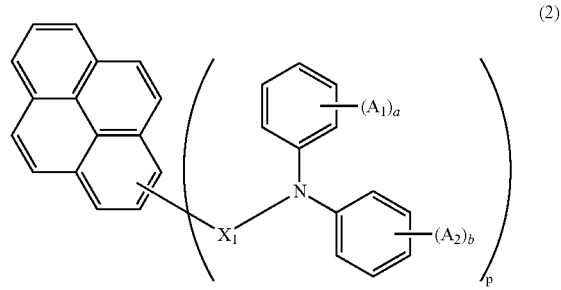

(2)

Furthermore, the aromatic amine derivative represented by the general formula (1) is preferably of a structure represented by the following general formula (3).

[Chem. 4]

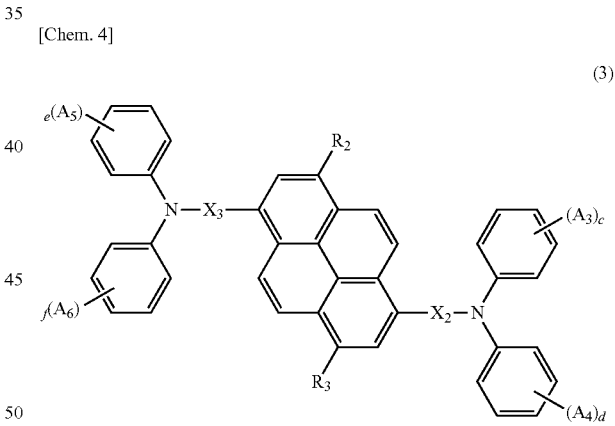

(3)

In the general formula (3), $A_3$ to $A_6$ and $R_2$ to $R_3$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 6 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted heterocyclic group having 5 to 50 carbon atoms, or a halogen atom. $A_3$ and $A_4$, and $A_5$ and $A_6$ may bind to each other to form a saturated or unsaturated ring.

c, d, e, and f each represent an integer of 0 to 5, preferable 0 to 3, and multiple $A_3$s, $A_4$s, $A_5$s, and $A_6$s may be identical to or different from each other, and may bind to each other to form a saturated or unsaturated ring when c, d, e, and f each represent 2 or more.

$X_2$ and $X_3$ each independently represent a substituted or unsubstituted arylene group having 5 to 50 carbon atoms.

Specific examples of: each of the groups represented by $A_3$ to $A_6$, and $R_2$ and $R_3$; a substituent; and a ring which $A_3$ and $A_4$, $A_5$ and $A_6$, or multiple $A_3$s, multiple $A_4$s, multiple $A_5$, and multiple $A_6$ may form include the same examples as those of $A_1$, $A_2$, and $R_1$ of the general formula (1).

Examples of the arylene group represented by each of $X_2$ and $X_3$ include the same groups as those of $X_1$ of the general formula (1).

The aromatic amine derivative of the present invention is preferably a material for an organic EL device, or is more preferably a hole-injecting material for an organic EL device or a doping material for an organic EL device.

Specific examples of the aromatic amine derivative represented by each of the general formulae (1) to (3) of the present invention are shown below. However, the aromatic amine derivative is not limited to these exemplified compounds.

Compound (1)

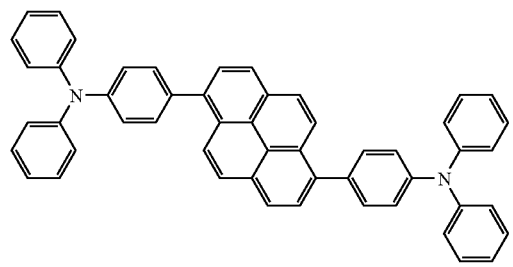

Compound (2)

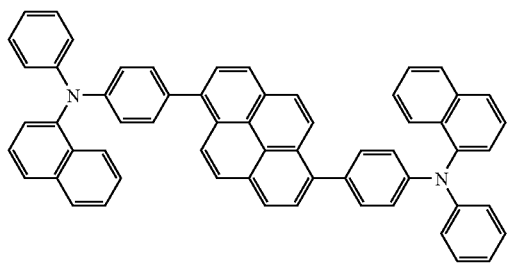

Compound (3)

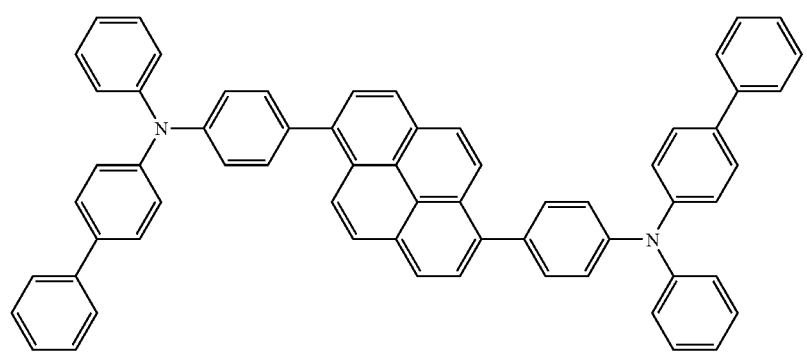

Compound (4)

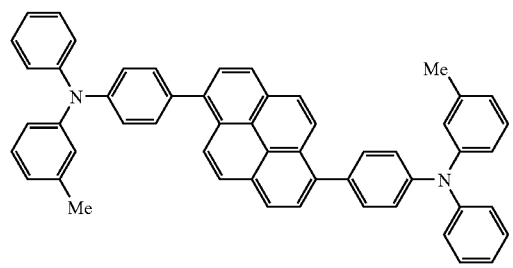

Compound (5)

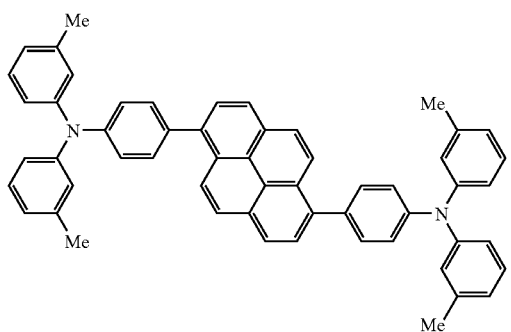

Compound (6)

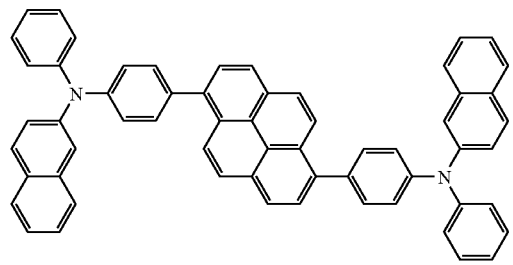

Compound (7)

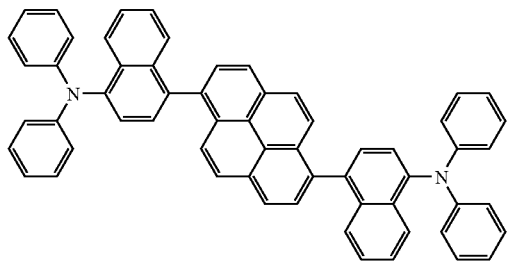

-continued
Compound (8)
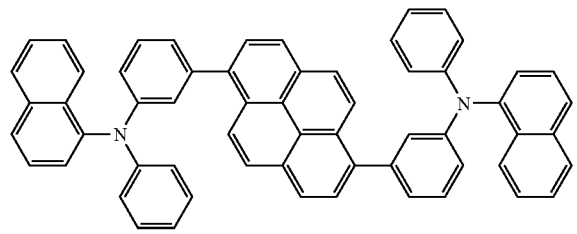
Compound (9)
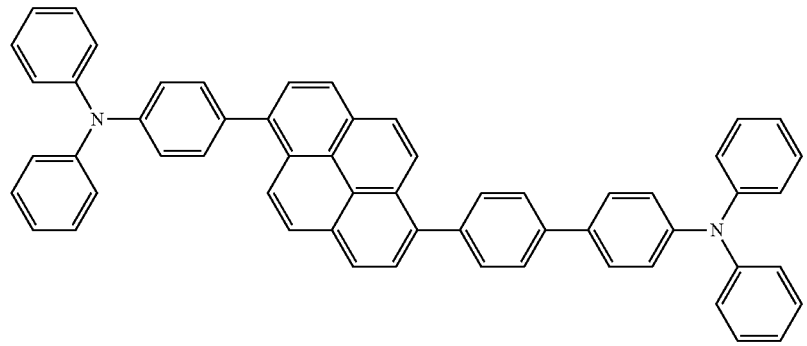
Compound (10)
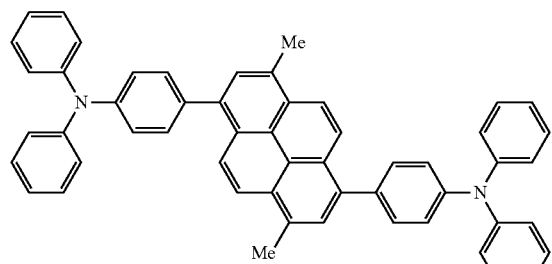
Compound (11)
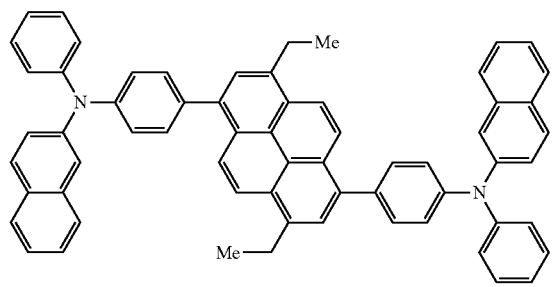
Compound (12)
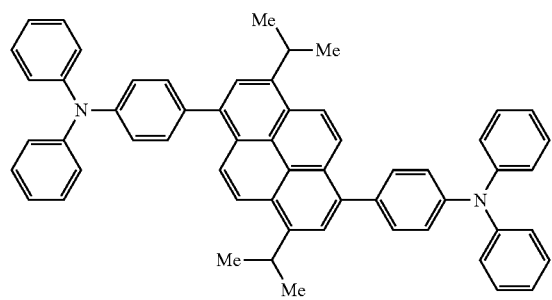
Compound (13)
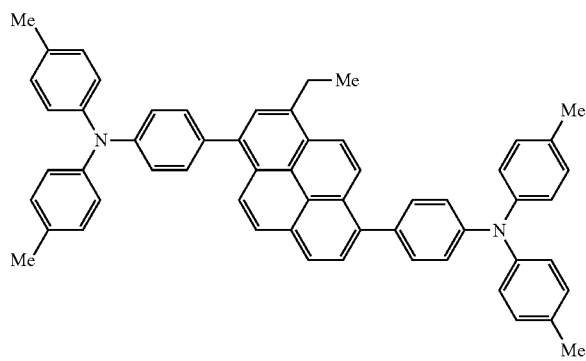
Compound (14)
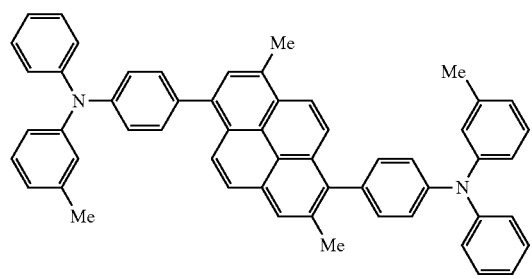
Compound (15)
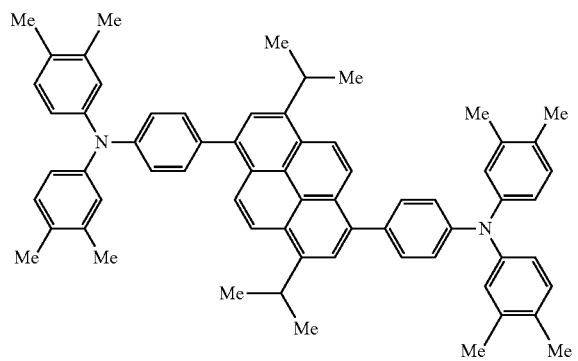

-continued
Compound (16)
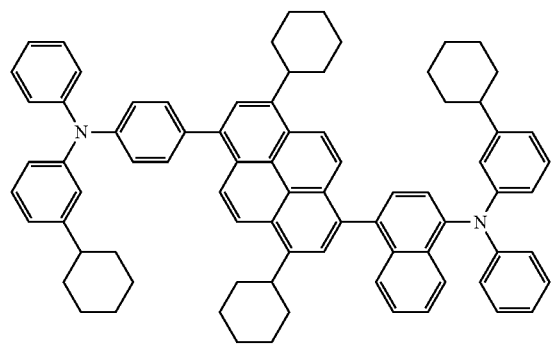
Compound (17)
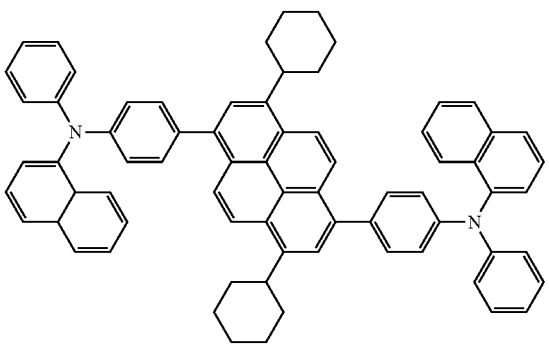
Compound (18)
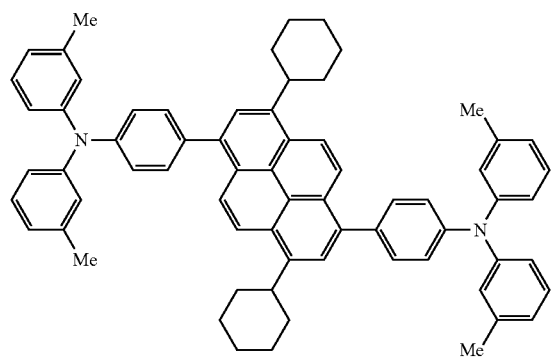
Compound (19)
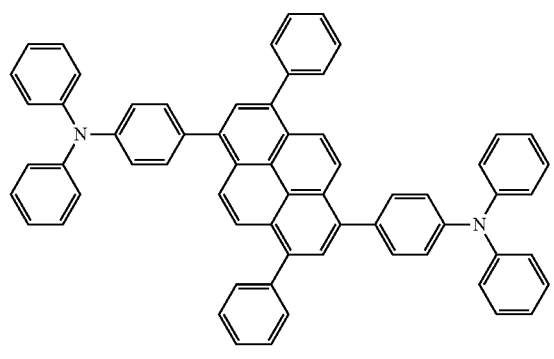
Compound (20)
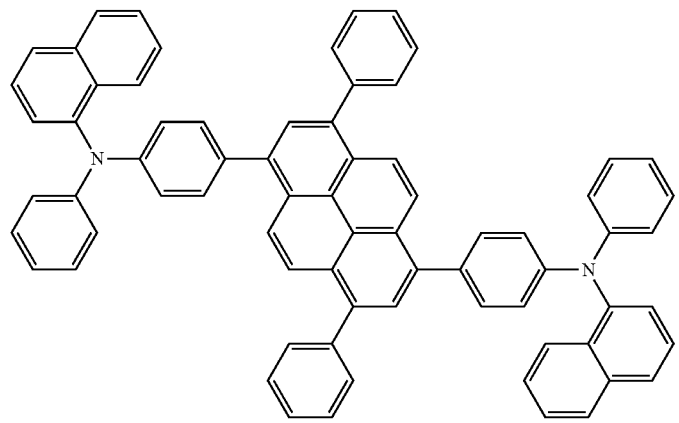
Compound (21)
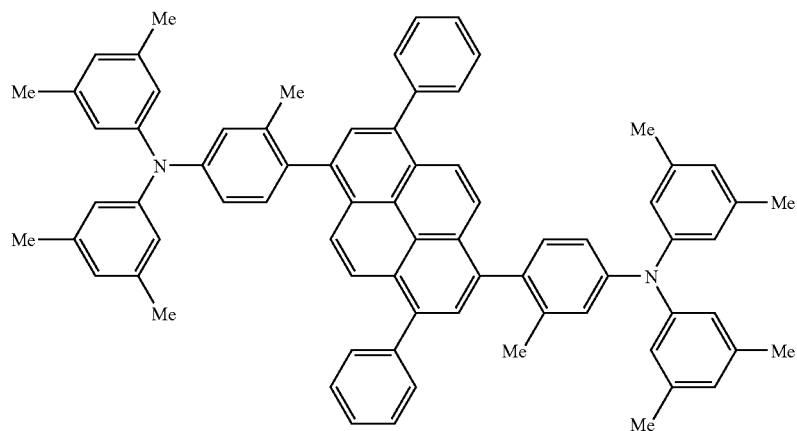

Compound (22)
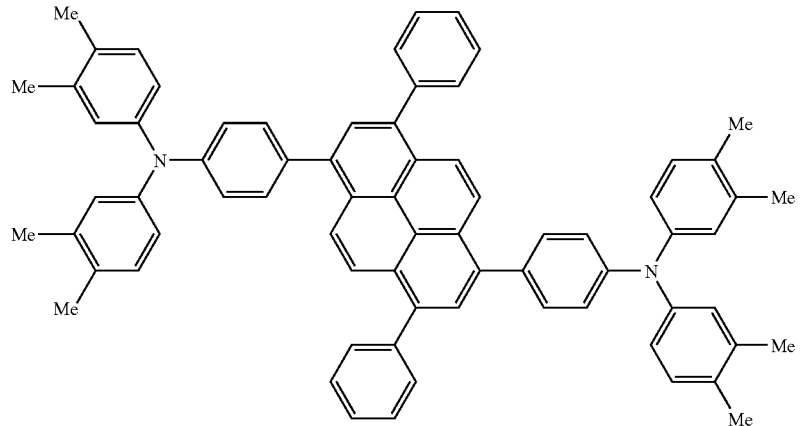
Compound (23)
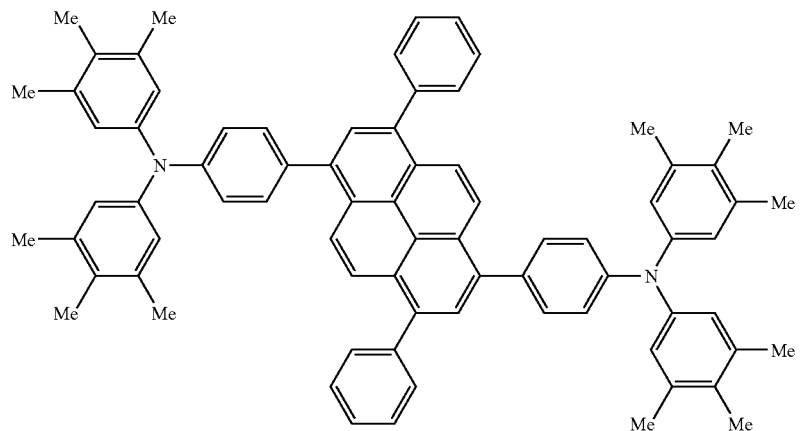
Compound (24)
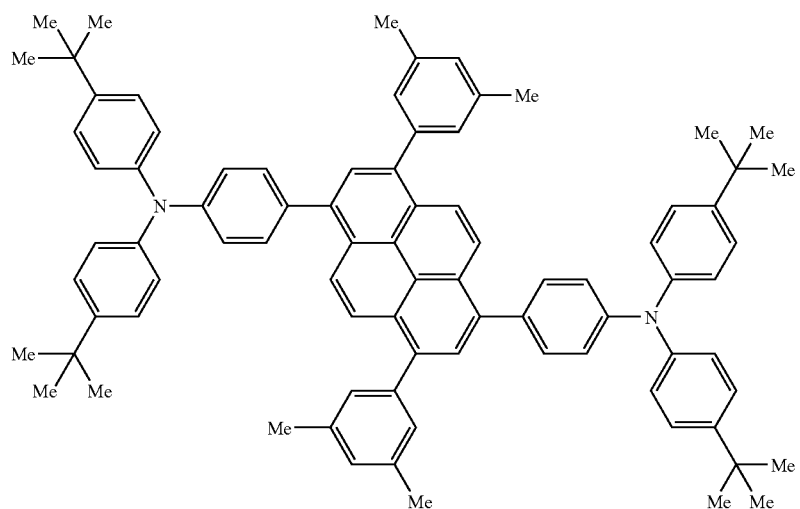

-continued
Compound (25)
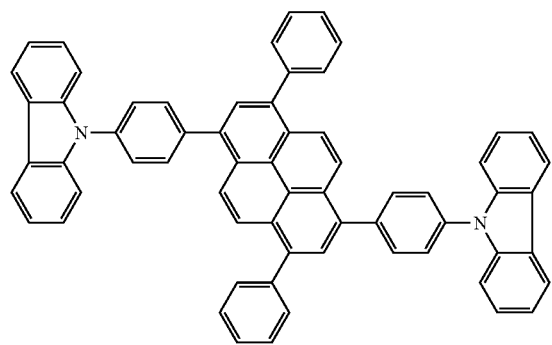
Compound (26)
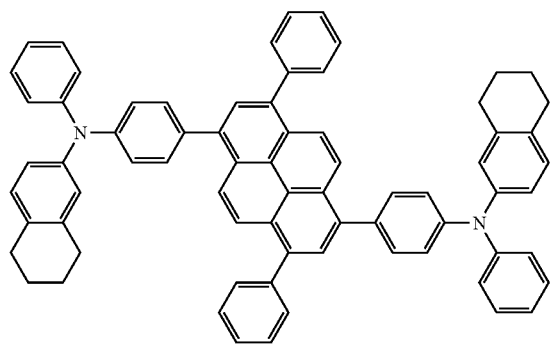
Compound (27)
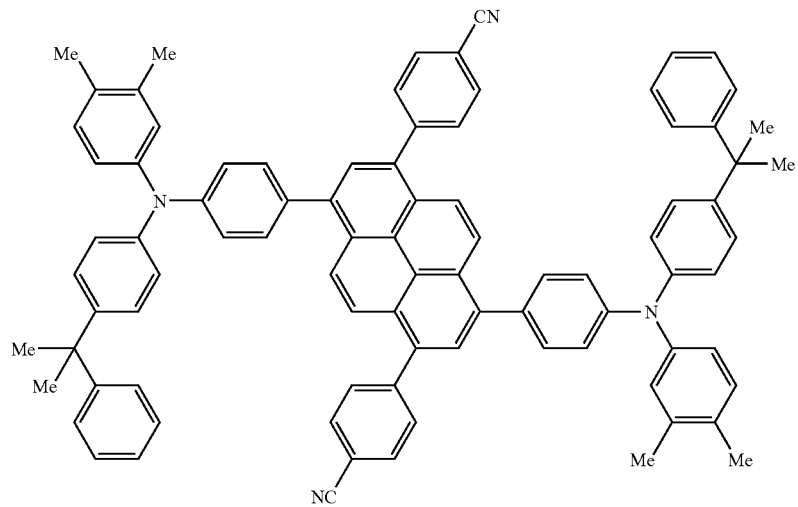
Compound (28)
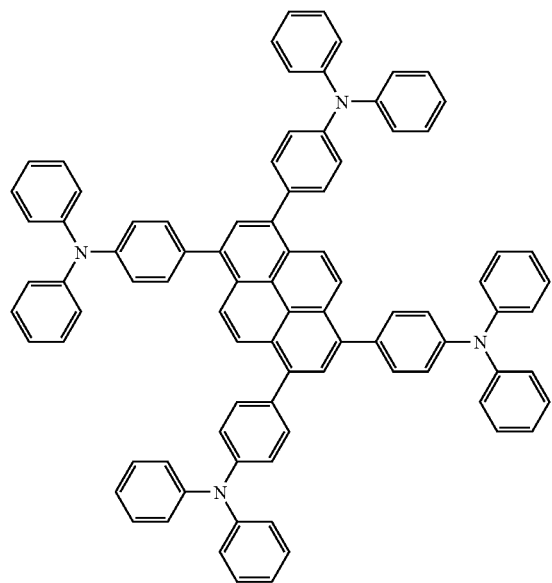
Compound (29)
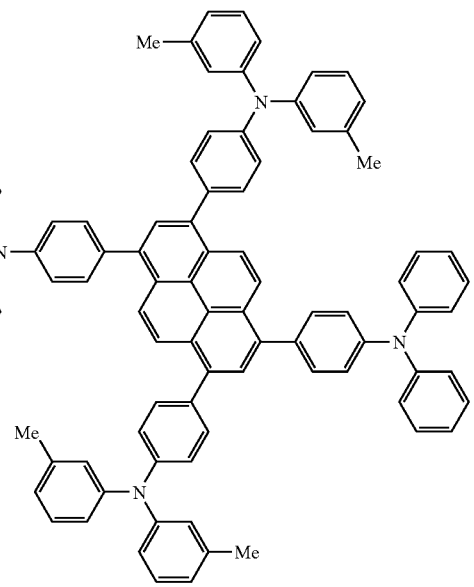

-continued
Compound (30)
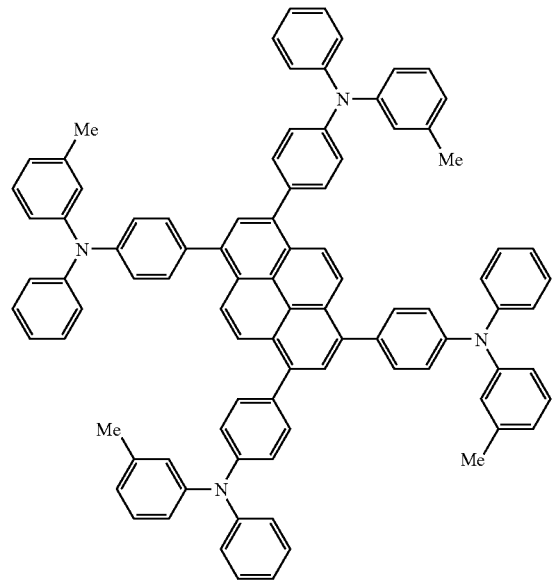
Compound (31)
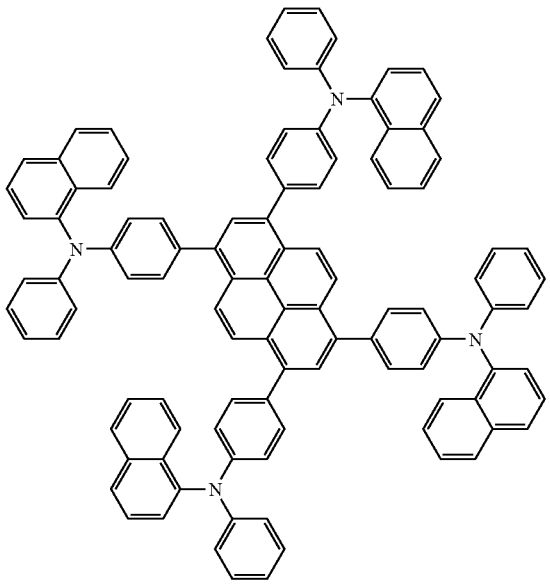
Compound (32)
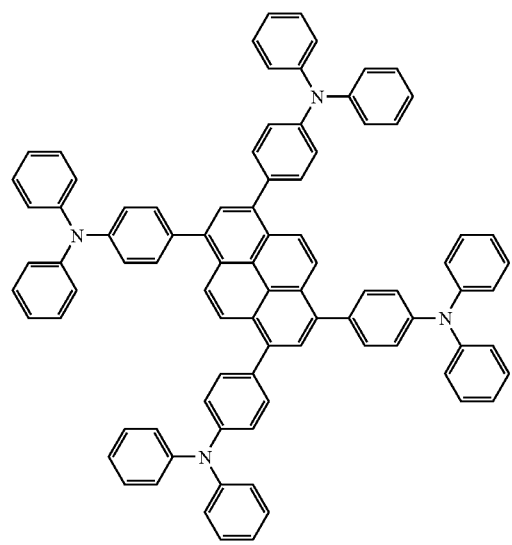
Compound (33)
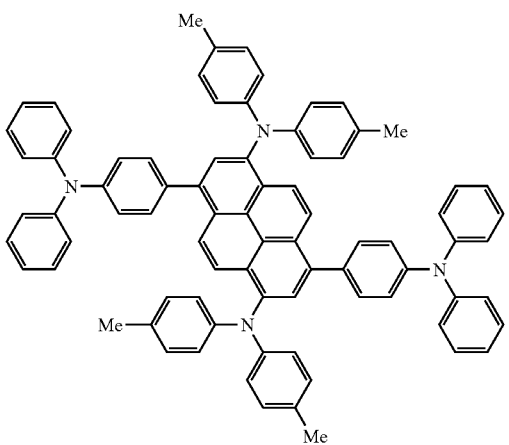

-continued
Compound (34)
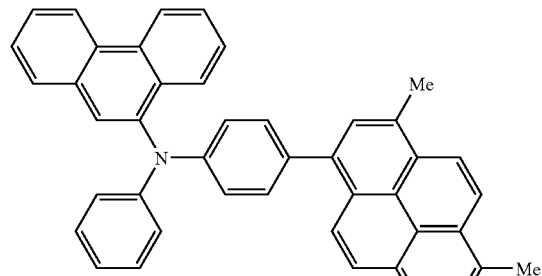
Compound (35)
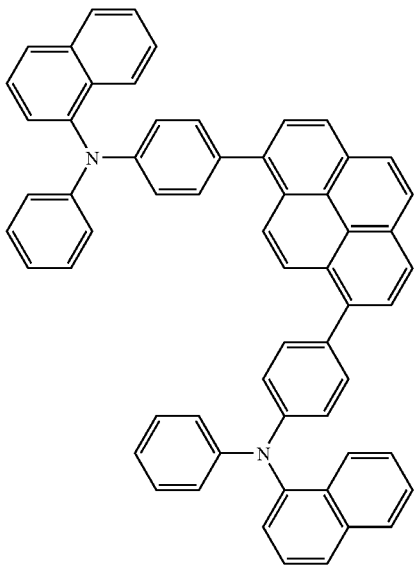
Compound (36)
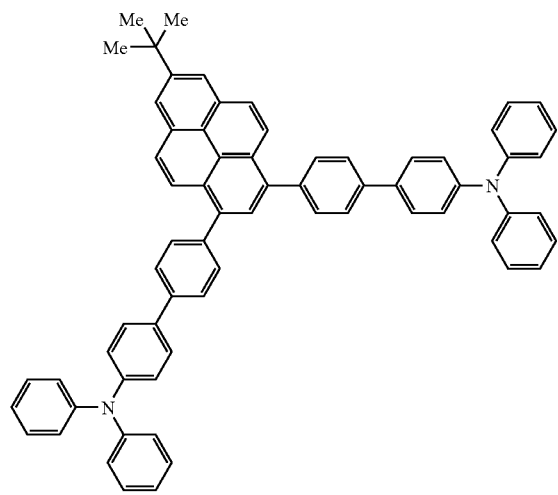
Compound (37)
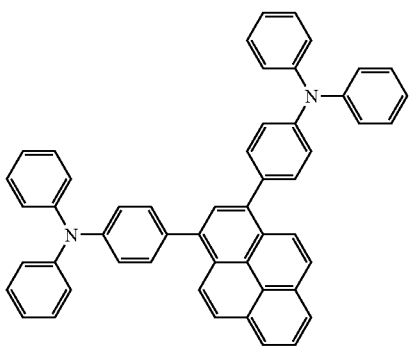
Compound (38)
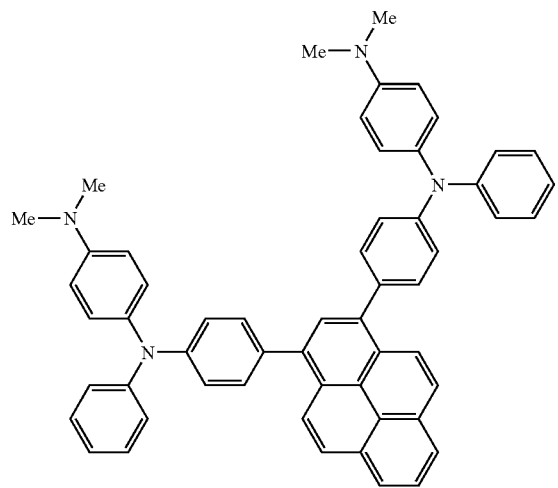
Compound (39)
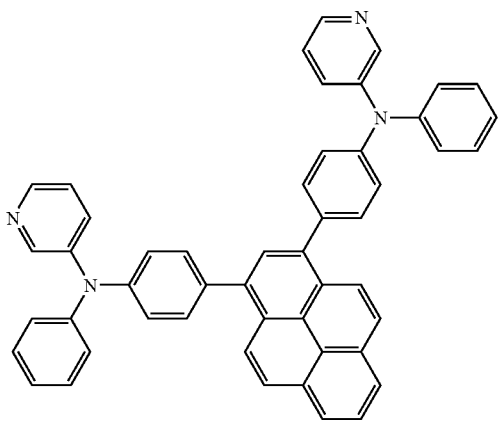

Next, a method of producing the aromatic amine derivative of the present invention will be described.

A method of producing the aromatic amine derivative represented by the general formula (1) of the present invention is not particularly limited, and the derivative may be produced by means of a known method. For example, the aromatic amine derivative is produced by means of palladium coupling (Suzuki reaction) among a 1,6-dibromopyrene body, a derivative (Journal of Chemical Society Perkin 1, p. 1622 (1972), Journal of Materials Chemistry, vol. 10, p. 315-319 (2000)), and an arylamine boronic acid.

Next, the organic EL device of the present invention will be described.

The organic EL device of the present invention includes: a cathode; an anode; and one or multiple organic thin film layers including at least a light-emitting layer, the one or multiple organic thin film layers being interposed between the cathode and the anode, in which at least one layer of the one or multiple organic thin film layers contains the aromatic amine derivative of the present invention alone or as a component of a mixture.

It is preferable that, in the organic EL device of the present invention, the one or multiple organic thin film layers have a hole-injecting layer, and the hole-injecting layer contains the aromatic amine derivative of the present invention alone or as a component of a mixture. Further, it is preferable that the main component of the hole-injecting layer is the aromatic amine derivative of the present invention.

Further, it is more preferable that, in the organic EL device of the present invention, the light-emitting layer contains the aromatic amine derivative of the present invention alone or as a component of a mixture. It is still more preferable that the light-emitting layer contains the aromatic amine derivative of the present invention as a doping material, and even more preferable that it contains the aromatic amine derivative at 0.1 to 20 weight %.

The aromatic amine derivative of the present invention is particularly preferable as an organic EL device emitting blue-based light.

In the present invention, the organic EL device having multiple organic thin film layers is a laminate having, for example, an (anode/hole-injecting layer/light-emitting layer/cathode), (anode/light-emitting layer/electron-injecting layer/cathode), or (anode/hole-injecting layer/light-emitting layer/electron-injecting layer/cathode) constitution.

In addition to the aromatic amine derivative of the present invention, an additional known light-emitting material, doping material, hole-injecting material, or electron-injecting material can be used as required in the multiple layers. When the organic EL device has the multiple organic thin film layers, a reduction in luminance or lifetime due to quenching can be prevented. If needed, a light-emitting material, a doping material, a hole-injecting material, and an electron-injecting material can be used in combination. In addition, a doping material can provide improvements in emission luminance and luminous efficiency, and red or blue light emission. In addition, each of the hole-injecting layer, the light-emitting layer, and the electron-injecting layer may be formed of a layer constitution having two or more layers. At that time, in the case of the hole-injecting layer, a layer for injecting a hole from the electrode is referred to as a hole-injecting layer, and a layer for receiving the hole from the hole-injecting layer and transporting the hole to the light-emitting layer is referred to as a hole-transporting layer. In the same manner, in the case of the electron-injecting layer, a layer for injecting an electron from the electrode is referred to as an electron-injecting layer, and a layer for receiving the electron from the electron-injecting layer and transporting the electron to the light-emitting layer is referred to as an electron-transporting layer. Each of those layers is selected and used depending on factors such as the energy level of a material, heat resistance, and adhesiveness between the layer and an organic layer or a metal electrode.

Examples of a host material or a doping material available for the light-emitting layer together with the aromatic amine derivative of the present invention include, but not limited to: for example, large amounts of fused aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethinyl)anthracene, and 1,4-bis(9'-ethinylanthracene)benzene and derivatives thereof; organic metal complexs such as tris(8-quinolinolato)aluminum or bis-(2-methyl-8-quinolinolato)-4-(phenylphenolinato)aluminum; a triarylamine derivative, a styrylamine derivative, a stilbene derivative, a coumarin derivative, a pyrane derivative, an oxazone derivative, a benzothiazole derivative, a benzoxazole derivative, a benzimidazole derivative, a pyrazine derivative, a cinnamate derivative, a diketopyrrolopyrrole derivative, an acridone derivative, and quinacridone derivative.

A compound having an ability of transporting a hole, having hole injection efficiency from an anode and excellent hole injection efficiency to a light-emitting layer or a light-emitting material, preventing the migration of an exciton generated in the light-emitting layer to an electron-injecting layer or an electron-injecting material, and having excellent thin film-formability is preferable as a hole-injecting material. Specific examples of the compound include, but not limited to, a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, hydrazone, acylhydrazone, polyarylalkane, stilbene, butadiene, benzidine type triphenylamine, styrylamine type triphenylamine, diamine type triphenylamine, derivatives thereof, and polymer materials such as polyvinyl carbazole, polysilane, and a conductive polymer.

Out of available hole-injecting materials in the organic EL device of the present invention, additional effective hole-injecting materials are an aromatic tertiary amine derivative and a phthalocyanine derivative.

An example of the aromatic tertiary amine derivative includes, but not limited to, for example, triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, or N,N-bis(4-di-4-tolylaminophenyl)-4-phenyl-cyclohexane, or an oligomer or a polymer having those aromatic tertiary amine skeletons.

Examples of the phthalocyanine (Pc) derivative include, but not limited to, for example, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc—O—GaPc, and naphthalocyanine derivatives.

In addition, the organic EL device of the present invention is preferably formed of a layer containing each of those aromatic tertiary amine derivatives and/or each of phthalocyanine derivatives between a light-emitting layer and an anode, for example, the hole-transporting layer or the hole-injecting layer.

A compound having an ability of transporting electrons, having electron injection efficiency from a cathode and excellent electron injection efficiency to a light-emitting layer or a light-emitting material, preventing the migration of an exciton generated in the light-emitting layer to the hole-injecting layer, and having excellent thin film-formability is preferable as an electron-injecting material. Specific examples of the compound include fluorenone, anthraquinodimethane, diphenoquinone, thiopyranedioxide, oxazole, oxadiazole, triazole, imidazole, perylenetetracarboxylic acid, fluorenylidenemethane, anthraquinodimethane, anthrone, and derivatives thereof, but the compound is not limited thereto. In addition, an electron-accepting substance can be added to the hole-injecting material or an electron-donating substance can be added to the electron-injecting material to thereby intensify the hole-injecting material or the electron-injecting material, respectively.

In the organic EL device of the present invention, additional effective electron-injecting materials are a metal complex compound and a nitrogen-containing five-membered ring derivative.

Examples of the metal complex compound include, but not limited to, for example, 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, and bis(2-methyl-8-quinolinato)(2-naphtholato)gallium.

Examples of the preferred nitrogen-containing five-memebered derivative include, for example, an oxazole derivative, a thiazole derivative, an oxadiazole derivative, a thiadiazole derivative, and a triazole derivative. Specific examples of the derivative include, but not limited to, 2,5-bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, and 1,4-bis[2-(5-phenyltriazolyl)]benzene.

In the organic EL device of the present invention, in addition to the aromatic amine derivative, at least one kind of a light-emitting material, a doping material, a hole-injecting material, and an electron-injecting material may be incorporated into any one of the organic thin film layers. In addition, the surface of the organic EL device obtained according to the present invention can be provided with a protective layer, or the entire device can be protected with silicone oil, a resin, or the like with a view to improving the stability of the device against temperature, humidity, an atmosphere, or the like.

A conductive material having a work function larger than 4 eV is suitably used in the anode of the organic EL device of the present invention. Examples of an available conductive material include: carbon, aluminum, vanadium, iron, cobalt, nickel, tungsten, silver, gold, platinum, and palladium, and alloys of them; metal oxides such as tin oxide and indium oxide to be used in an ITO substrate and an NESA substrate; and organic conductive resins such as polythiophene and polypyrrole. A conductive substance having a work function smaller than 4 eV is suitably used in the cathode of the device.

Examples of an available conductive substance include, but not limited to, magnesium, calcium, tin, lead, titanium, yttrium, lithium, ruthenium, manganese, aluminum, and lithium fluoride, and alloys of them. Representative examples of the alloys include, but not limited to, a magnesium/silver alloy, a magnesium/indium alloy, and a lithium/aluminum alloy. A ratio between the components of an alloy is controlled depending on, for example, the temperature of a deposition source, an atmosphere, and the degree of vacuum, and is selected to be an appropriate ratio. Each of the anode and the cathode may be formed of a layer constitution having two or more layers if needed.

At least one surface of the organic EL device of the present invention is desirably sufficiently transparent in the luminous wavelength region of the device so that the device can efficiently emit light. A substrate is also desirably transparent. A transparent electrode is formed by means of any one of the above conductive materials, and is set by means of a method such as deposition or sputtering in such a manner that desired translucency is secured. The light transmittance of an electrode on a light-emitting surface is desirably 10% or more. The substrate is not limited as long as it has mechanical strength, thermal strength, and transparency. Examples of the substrate include a glass substrate and a transparent resin film. Examples of the transparent resin film include polyethylene, an ethylene-vinyl acetate copolymer, an ethylene-vinyl alcohol copolymer, polystyrene, polymethyl methacrylate, polyvinyl chloride, polyvinyl alcohol, polyvinyl butyral, nylon, polyether ether ketone, polysulfone, polyether sulfone, a tetrafluoroethylene-perfluoroalkyl vinyl ether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyether imide, polyimide, and polypropylene.

Any one of: dry film forming methods such as vacuum deposition, sputtering, plasma, and ion plating; and wet film forming methods such as spin coating, dipping, and flow coating is applicable to the formation of each layer of the organic EL device according to the present invention. The thickness of each layer is not particularly limited, but must be set to an appropriate thickness. An excessively thick thickness requires an increased applied voltage for obtaining certain optical output, thereby resulting in poor efficiency. An excessively thin thickness causes a pin hole or the like, so sufficient emission luminance cannot be obtained even when an electric field is applied. In general, the thickness is in the range of preferably 5 nm to 10 μm, or more preferably 10 nm to 0.2 μm.

In the case of a wet film forming method, a material of which each layer is formed is dissolved or dispersed into an appropriate solvent such as ethanol, chloroform, tetrahydrofuran, or dioxane, to thereby form a thin film. At that time, any one of the above solvents may be used. In addition, an appropriate resin or additive may be used in each of the organic thin film layers for, for example, improving film formability or preventing a pin hole in the layer. Examples of an available resin include: insulating resins such as polystyrene, polycarbonate, polyallylate, polyester, polyamide, polyurethane, polysulfone, polymethyl methacrylate, polymethyl acrylate, and cellulose, and copolymers of them; photoconductive resins such as poly-N-vinylcarbazole and polysilane; and conductive resins such as polythiophene and polypyrrole. Examples of the additive include an antioxidant, a UV absorber, and a plasticizer.

The organic EL device of the present invention can find use in applications including: a flat luminous body such as the flat panel display of a wall hanging television; a light source for the backlight, meters, or the like of a copying machine, a printer, or a liquid crystal display; a display panel; and a signal lamp. In addition, the material of the present invention can be used in not only the field of an organic EL device but also the fields of an electrophotographic photosensitive member, a photoelectric conversion element, a solar cell, and an image sensor.

EXAMPLES

Next, the present invention will be described in more detail by way of examples. However, the present invention is not limited to these examples.

Synthesis Example 1

Synthesis of Compound (1)

In a stream of argon, 5.2 g (14 mmol) of 1,6-dibromopyrene, 10 g (35 mmol) of 4-(diphenylamino)phenyl boronic acid, 0.8 g (0.7 mmol) of tetrakistriphenylphosphine palladium, an aqueous solution containing 7 g (65 mmol) of sodium carbonate in 33 mL of water, and 70 mL of toluene were added to a 300-mL three-necked flask equipped with a cooling pipe, and the whole was refluxed under heat for 8 hours. After the completion of the reaction, a precipitated crystal was filtered out and washed with 50 mL of toluene and 100 mL of methanol. The resultant coarse crystal was recrystallized with toluene, whereby 8 g of a white crystal were obtained. The crystal was identified as Compound (1) through the measurement of a $^1$H-NMR spectrum (FIG. 1) and a field desorption-mass spectrum (FD-MS) (80% yield). The $^1$H-NMR spectrum was measured by means of a DRX-500 (a heavy methylene chloride solvent) manufactured by Brucker (the same holds true for the following synthesis examples). The maximum absorption wavelength and maximum fluorescent wavelength of the resultant compound measured in a toluene solution were 380 nm and 450 nm, respectively.

Synthesis Example 2

Synthesis of Compound (12)

Figure 2:
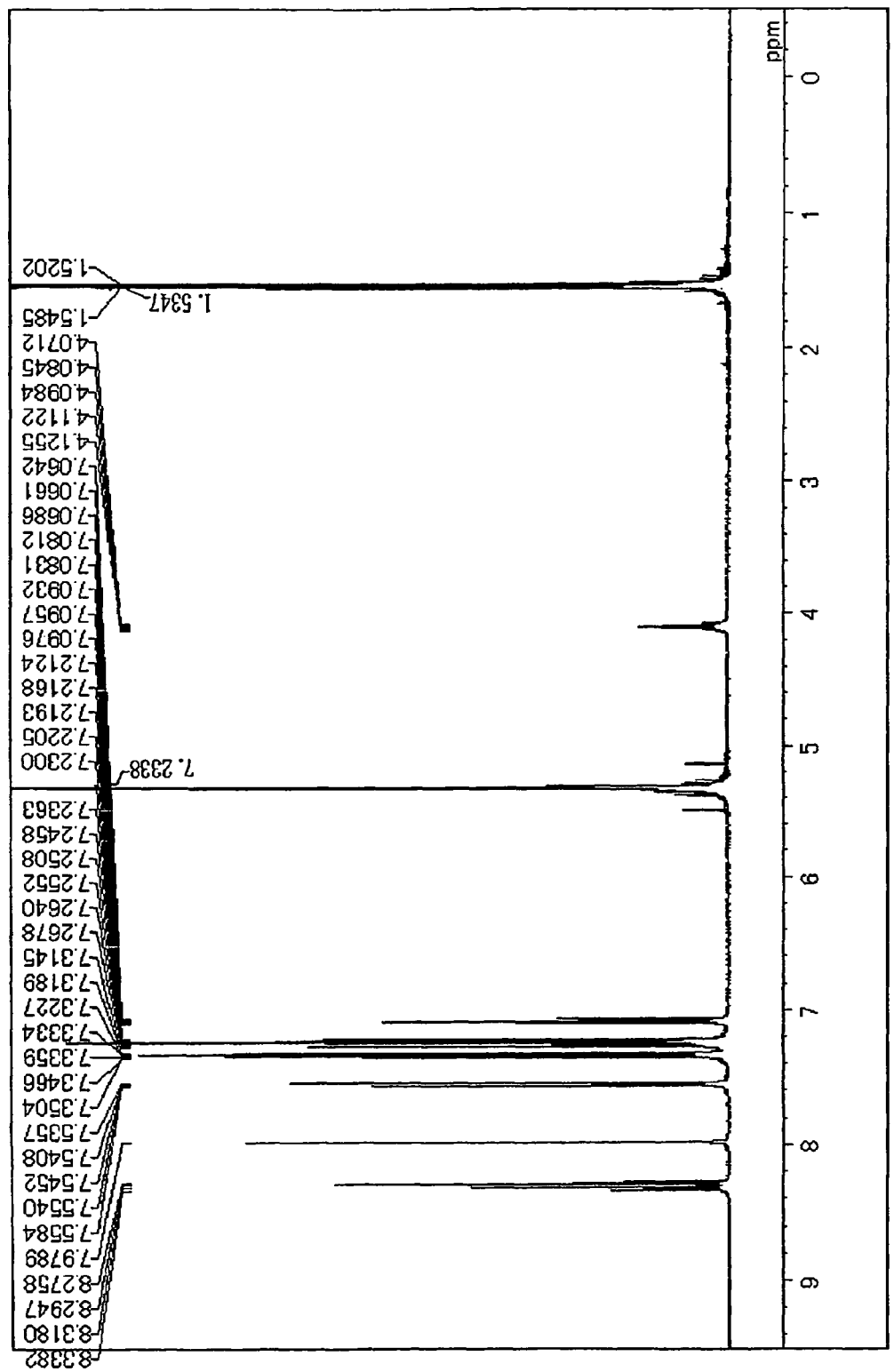
FIG. 2 A view showing the $^1$H-NMR spectrum of Compound (12) obtained in Synthesis Example 2.

In a stream of argon, 5.8 g (13 mmol) of 1,6-diisopropyl-3,8-dibromopyrene, 9 g (31 mmol) of 4-(diphenylamino)phenyl boronic acid, 0.8 g (0.7 mmol) of tetrakistriphenylphosphine palladium, an aqueous solution containing 4 g (65 mmol) of sodium carbonate in 20 mL of water, 30 mL of toluene, and 20 mL of dimethoxyethane were added to a 300-mL three-necked flask equipped with a cooling pipe, and the whole was refluxed under heat for 8 hours. After the completion of the reaction, a precipitated crystal was filtered out and washed with 50 mL of toluene and 100 mL of methanol. The resultant coarse crystal was recrystallized with toluene, whereby 5 g of a white crystal were obtained. The crystal was identified as Compound (12) through the measurement of a $^1$H-NMR spectrum (FIG. 2) and a FD-MS (80% yield). The maximum absorption wavelength and maximum fluorescent wavelength of the resultant compound measured in a toluene solution were 390 nm and 452 nm, respectively.

Synthesis Example 3

Synthesis of Compound (15)

(1) Synthesis of 1,6-diisopropyl-3,8-di(4-chlorophenyl)pyrene

In a stream of argon, 4.4 g (10 mmol) of 1,6-diisopropyl-3,8-dibromopyrene, 3.6 g (23 mmol) of 4-chlorophenyl boronic acid, 0.6 g (0.5 mmol) of tetrakistriphenylphosphine palladium, an aqueous solution containing 5 g (65 mmol) of sodium carbonate in 23 mL of water, and 45 mL of toluene were added to a 300-mL three-necked flask equipped with a cooling pipe, and the whole was refluxed under heat for 8 hours. After the completion of the reaction, an organic layer was washed with water and dried with magnesium sulfate. After that, the solvent was distilled off by means of a rotary evaporator. Thus, 5 g of 1,6-diisopropyl-3,8-di(4-chlorophenyl)pyrene of interest were obtained (a yellow crystal, 80% yield).

(2) Synthesis of Compound (15)

Figure 3:
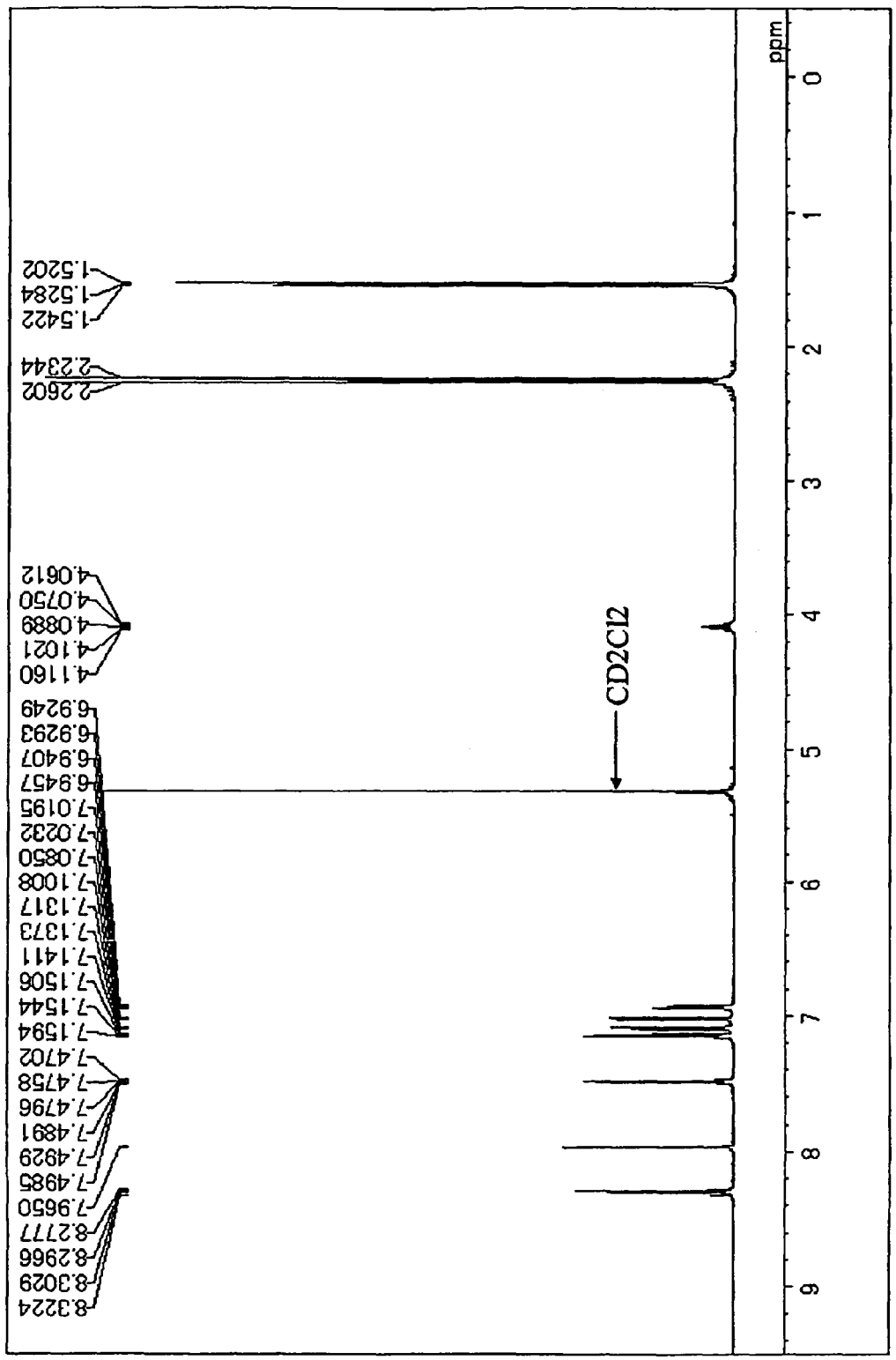
FIG. 3 A view showing the $^1$H-NMR spectrum of Compound (15) obtained in Synthesis Example 3.

In a stream of argon, 4.5 g (9 mmol) of 1,6-diisopropyl-3,8-di(4-chlorophenyl)pyrene, 4.2 g (19 mmol) of bis(3,4-dimethylphenyl)amine, 0.1 g (1.5 mol %) of palladium acetate, 0.06 g (3 mol %) of tri-t-butylphosphine, 1.7 g (18 mmol) of t-butoxysodium, and 80 mL of dry toluene were added to a 300-mL three-necked flask equipped with a cooling pipe. After that, the mixture was stirred under heat at 100° C. overnight. After the completion of the reaction, a precipitated crystal was filtered out and washed with 50 mL of toluene and 100 mL of methanol. As a result, 7.8 g of a pale yellow powder were obtained. The powder was identified as Compound (15) through the measurement of a $^1$H-NMR spectrum (FIG. 3) and an FD-MS (95% yield). The maximum absorption wavelength and maximum fluorescent wavelength of the resultant compound measured in a toluene solution were 393 nm and 458 nm, respectively.

Synthesis Example 4

Synthesis of Compound (19)

(1) Synthesis of 1,6-diphenylpyrene

In a stream of argon, 20 g (55.6 mmol) of 1,6-dibromopyrene, 16.3 g (133 mmol) of phenyl boronic acid, 2.5 g (4 mol %) of tetrakistriphenylphosphine palladium, an aqueous solution containing 26.5 g (65 mmol) of sodium carbonate in 125 mL of water, and 250 mL of toluene were added to a 1-L three-necked flask equipped with a cooling pipe, and the whole was refluxed under heat at 100° C. for 8 hours. After the completion of the reaction, 50 mL of water was added and then a crystal was filtered out, washed with 50 mL of water, 100 mL of ethanol, and 100 mL of toluene. As a result, 15.3 g of 1,6-diphenylpyrene (a white powder) was obtained (99% yield).

(2) Synthesis of 1,6-diphenyl-3,8-dibromopyrene

In a stream of argon, 15.3 g (43.2 mmol) of 1,6-diphenylpyrene, 23 g (130 mmol) of N-bromosuccinimide, and 600 mL of dry dimethylformamide (DMF) were added to a 1-L round-bottomed flask equipped with a cooling pipe. After that, the mixture was stirred under heat at 50° C. for 8 hours. After the completion of the reaction, 300 mL of water were added, and then a crystal was filtered out and washed with 50 mL of water and 100 mL of methanol. As a result, 16.3 g of 1,6-diphenyl-3,8-dibromopyrene (a pale yellow powder) were obtained (95% yield).

(3) Synthesis of Compound (19)

Figure 4:
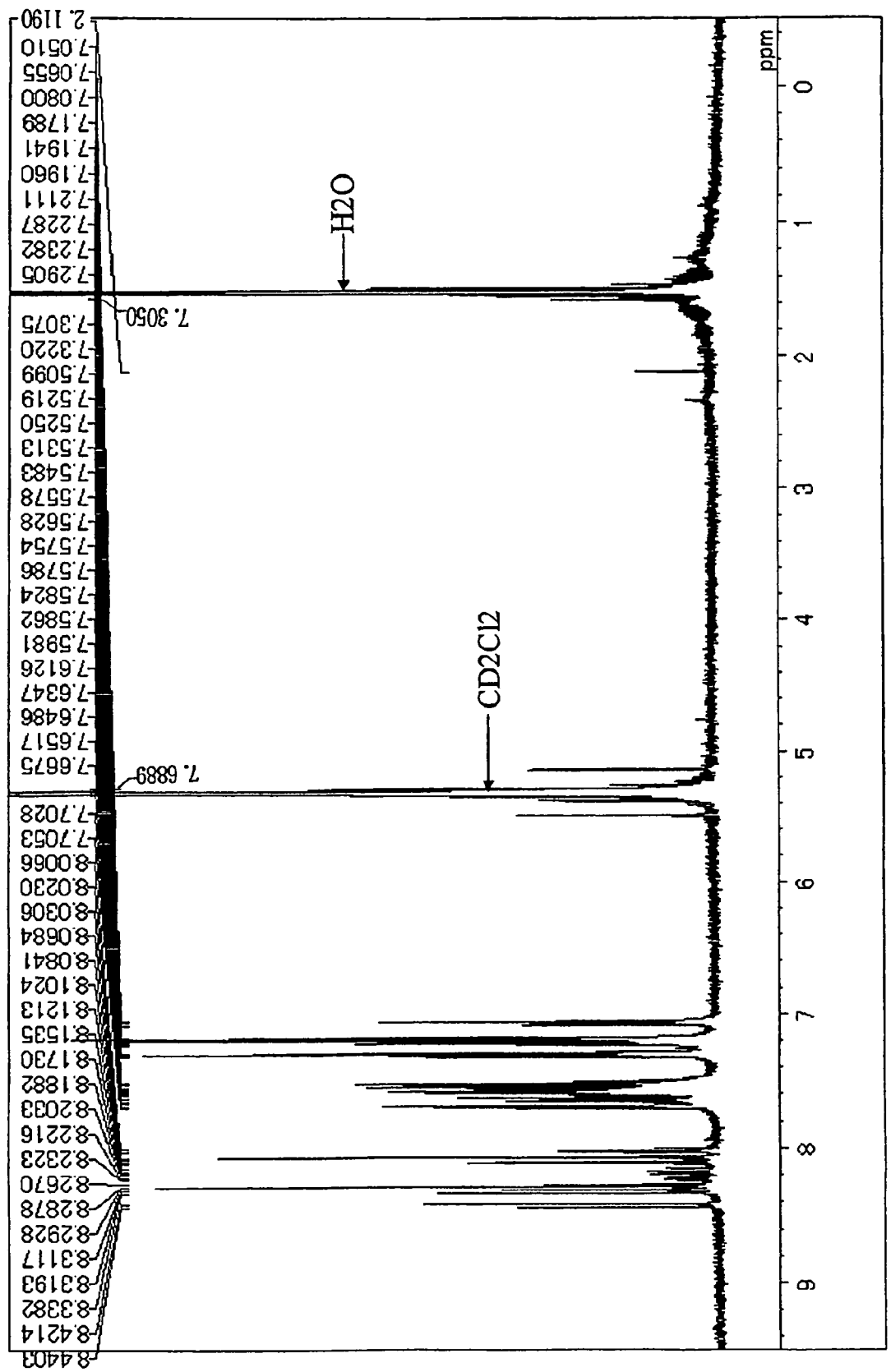
FIG. 4 A view showing the $^1$H-NMR spectrum of Compound (19) obtained in Synthesis Example 4.

In a stream of argon, 6.1 g (12 mmol) of 1,6-diphenyl-3,8-dibromopyrene, 8.3 g (29 mmol) of 4-(diphenylamino)phenyl boronic acid, 0.7 g (0.6 mmol) of tetrakistriphenylphosphine palladium, an aqueous solution containing 5.1 g (48 mmol) of sodium carbonate in 24 mL of water, 60 mL of toluene, and 30 mL of dimethoxyethane were added to a 500-mL three-necked flask equipped with a cooling pipe, and the whole was refluxed under heat at 100° C. overnight. After the completion of the reaction, a precipitated crystal was filtered out and washed with 50 mL of toluene and 100 mL of methanol. As a result, 5.7 g of a pale yellow powder were obtained. The powder was identified as Compound (19) through the measurement of a $^1$H-NMR spectrum (FIG. 4) and a FD-MS (57% yield). The maximum absorption wavelength and maximum fluorescent wavelength of the resultant compound measured in a toluene solution were 396 nm and 463 nm, respectively.

Synthesis Example 5

Synthesis of Compound (22)

(1) Synthesis of 1,6-diphenyl-3,8-di(4-chlorophenyl)pyrene

In a stream of argon, 5.7 g (11 mmol) of 1,6-diphenyl-3,8-dibromopyrene, 4.1 g (27 mmol) of 4-chlorophenyl boronic acid, 0.6 g (0.5 mmol) of tetrakistriphenylphosphine palladium, an aqueous solution containing 5.3 g (50 mmol) of sodium carbonate in 30 mL of water, and 100 mL of toluene were added to a 500-mL three-necked flask equipped with a cooling pipe, and the whole was refluxed under heat for 8 hours. After the completion of the reaction, an organic layer was washed with water and dried with magnesium sulfate. After that, the solvent was distilled off by means of a rotary evaporator. Thus, 6.3 g of 1,6-diphenyl-3,8-di(4-chlorophenyl)pyrene of interest were obtained (a yellow crystal, 99% yield).

(2) Synthesis of Compound (22)

Figure 5:
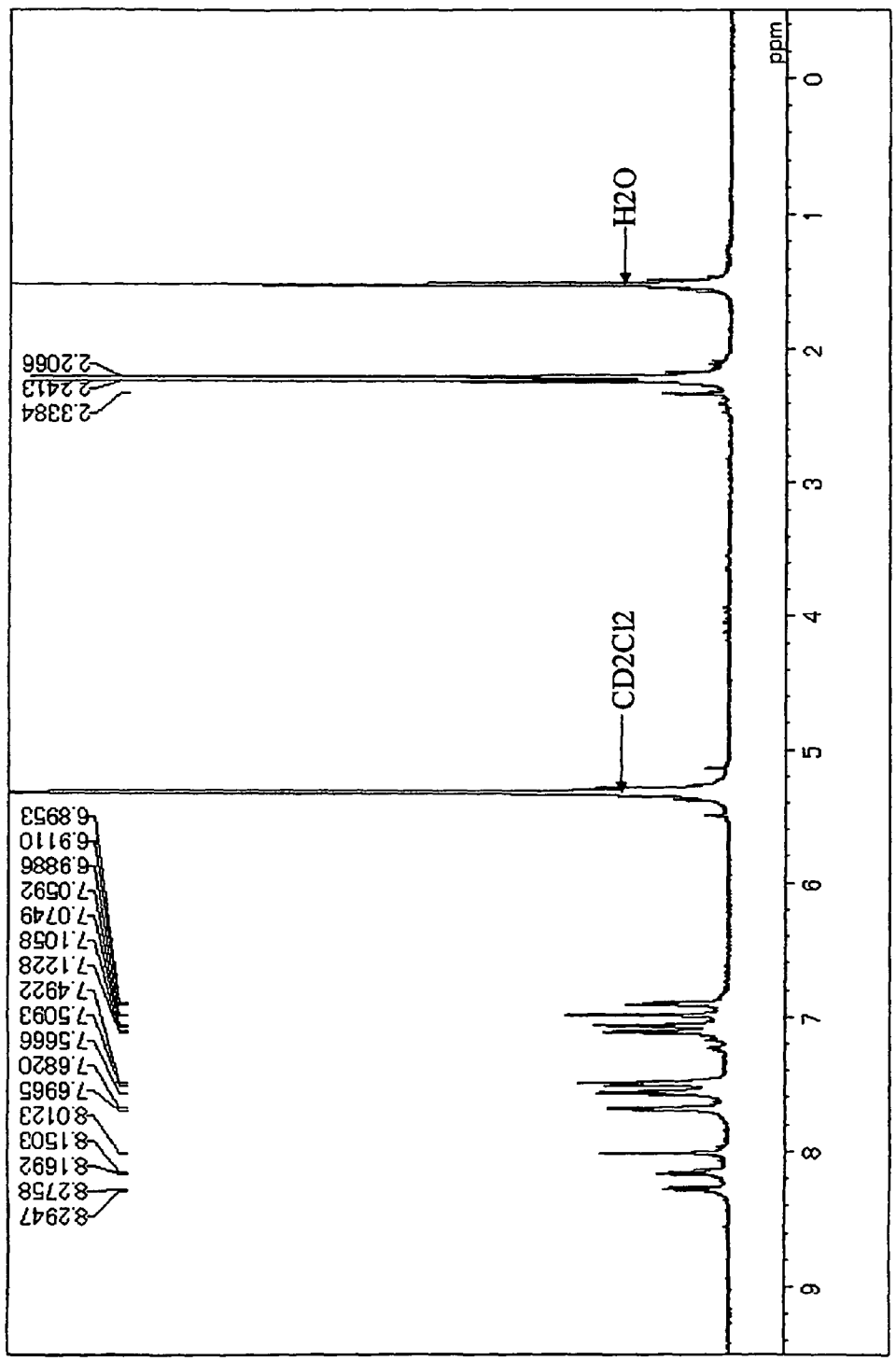
FIG. 5 A view showing the $^1$H-NMR spectrum of Compound (22) obtained in Synthesis Example 5.

In a stream of argon, 6.3 g (11 mmol) of 1,6-diphenyl-3,8-di(4-chlorophenyl)pyrene, 5.2 g (23 mmol) of bis(3,4-dimethylphenyl)amine, 0.1 g (1.5 mol %) of palladium acetate, 0.06 g (3 mol %) of tri-t-butylphosphine, 2.1 g (22 mmol) of t-butoxysodium, and 80 mL of dry toluene were added to a 300-mL three-necked flask equipped with a cooling pipe. After that, the mixture was stirred under heat at 100° C. overnight. After the completion of the reaction, a precipitated crystal was filtered out and washed with 50 mL of toluene and 100 mL of methanol. As a result, 8.3 g of a pale yellow powder were obtained. The powder was identified as Compound (22) through the measurement of a $^1$H-NMR spectrum (FIG. 5) and an FD-MS (80% yield). The maximum absorption wavelength and maximum fluorescent wavelength of the resultant compound measured in a toluene solution were 413 nm and 473 nm, respectively.

Example 1

(1) Production of Organic EL Device

A transparent electrode composed of an indium tin oxide having a thickness of 130 nm was arranged on a glass substrate measuring 25×75×1.1 mm. The glass substrate was subjected to ultrasonic cleaning in isopropyl alcohol, and was irradiated with ultraviolet light and ozone for cleaning.

Next, the glass substrate equipped with the transparent electrode was mounted on a substrate holder in the deposition tank of a vacuum deposition device. In addition, the degree of vacuum in a vacuum tank was reduced to $1 \times 10^{-3}$ Pa. After that, a hole-injecting layer, a hole-transporting layer, a light-emitting layer, an electron-transporting layer, an electron-injecting layer, and a cathode layer were sequentially laminated on an anode (transparent electrode) layer under the following deposition conditions, whereby an organic EL device was produced.

Hole-injecting layer: (material) Compound (1) described above; deposition condition 2 nm/sec; thickness 60 nm Hole-transporting layer: (material) N,N,N',N'-tetrakis(4-biphenyl)-4,4'-benzidine; deposition condition 2 nm/sec; thickness 20 nm Light-emitting layer: 10-(4-(naphthylen-1-yl)phenyl)-9-(naphthylen-2-yl)anthracene as a host material (deposition condition 2 nm/sec) and tetrakis(2-naphthyl)-4,4'-diaminostilbene as a dopant (deposition condition 0.2 nm/sec) are simultaneously deposited from the vapor; thickness 40 nm (weight ratio between the host material and the dopant is 40:2)

Electron-transporting layer: (material) tris(8-hydroxyquinolino)aluminum; deposition condition 2 nm/sec; thickness 20 nm Electron-injecting layer: (material) lithium fluoride; deposition condition 0.1 nm/sec; thickness 1 nm Cathode layer: (material) aluminum; deposition condition 2 nm/sec; thickness 200 nm (2) Evaluation of Organic EL Device The resultant device was subjected to an energization test. As a result, it was confirmed that emission luminance was 510 cd/m$^2$ at a voltage of 6.5 V and a luminescent color was blue. In addition, when the device was driven at a constant current with initial emission luminance set to 500 cd/m$^2$, a time period required for the luminance to reduce by 10% was 100 hours. Table 1 shows the obtained results. When the device was stored at 85° C. for 500 hours, no change in driving voltage was observed.

Examples 2 to 5

In each of the examples, an organic EL device was produced in the same manner as in Example 1 except that a material described in Table 1 was used instead of Compound (1) as a material for a hole-injecting layer.

Each of the resultant devices was evaluated in the same manner as in Example 1. As a result, as shown in Table 1, blue light emission was observed in each of all the devices. In addition, emission luminance was 460 to 520 cd/m$^2$, and a time period required for the luminance to reduce by 10% was 90 to 110 hours. When each of those devices was stored at 85° C. for 500 hours, no change in driving voltage was observed.

Comparative Example 1

An organic EL device was produced in the same manner as in Example 1 except that 4,4-bis(N,N-diphenylamino)terphenyl was used instead of Compound (1) as a material for a hole-injecting layer.

The resultant device was evaluated in the same manner as in Example 1. As a result, as shown in Table 1, blue light emission was observed. In addition, emission luminance was 300 cd/m$^2$, and a time period required for the luminance to reduce by 10% was 50 hours. When the device was stored at 85° C. for 500 hours, change in driving voltage by 2V or more was observed.

TABLE 1

| | Hole-injecting material | Driving voltage (V) | Luminescent color | Emission luminance (cd/m$^2$) | Time period required for luminance to reduce by 10% (hours) | Change in voltage after storage at 85° C. (for 500 hours) |
|---|---|---|---|---|---|---|
| Example 1 | (1) | 6.5 | Blue | 510 | 100 | No change |
| Example 2 | (2) | 6.5 | Blue | 520 | 110 | No change |
| Example 3 | (3) | 6.5 | Blue | 500 | 100 | No change |
| Example 4 | (4) | 6.5 | Blue | 490 | 100 | No change |
| Example 5 | (8) | 6.5 | Blue | 460 | 90 | No change |
| Comparative Example 1 | 4,4-bis(N,N-diphenylamino)terphenyl | 6.5 | Blue | 300 | 50 | 2 V or more |

Example 6

(1) Production of Organic EL Device

A transparent electrode composed of an indium tin oxide having a thickness of 130 nm was arranged on a glass substrate measuring 25×75×1.1 mm. The glass substrate was subjected to ultrasonic cleaning in isopropyl alcohol, and was irradiated with ultraviolet light and ozone for cleaning.

Next, the glass substrate equipped with the transparent electrode was mounted on a substrate holder in the deposition tank of a vacuum deposition device. In addition, the degree of vacuum in a vacuum tank was reduced to 1×10$^{-3}$ Pa. After that, a hole-injecting layer, a hole-transporting layer, a light-emitting layer, an electron-transporting layer, an electron-injecting layer, and a cathode layer were sequentially laminated on an anode (transparent electrode) layer under the following deposition conditions, whereby an organic EL device was produced.

Hole-injecting layer: (material) N',N"-bis [4-(diphenylamino)phenyl]-N',N"-diphenylbiphenyl-4,4'-diamine; deposition condition 2 nm/sec; thickness 60 nm Hole-transporting layer: (material) N,N,N',N'-tetrakis(4-biphenyl)-4,4'-benzidine; deposition condition 2 nm/sec; thickness 20 nm Light-emitting layer: 10-(4-(naphthylen-1-yl)phenyl)-9-(naphthylen-2-yl)anthracene as a host material (deposition condition 2 nm/sec) and the above compound (12) as a dopant (deposition condition 0.1 nm/sec) are simultaneously deposited from the vapor; thickness 40 nm (weight ratio between the host material and the dopant is 40:2)

Electron-transporting layer: (material) tris(8-hydroxyquinolino)aluminum; deposition condition 2 nm/sec; thickness 20 nm Electron-injecting layer: (material) lithium fluoride; deposition condition 0.1 nm/sec; thickness 1 nm Cathode layer: (material) aluminum; deposition condition 2 nm/sec; thickness 200 nm (2) Evaluation of Organic EL Device The resultant device was subjected to an energization test. As a result, it was confirmed that emission luminance was 500 cd/m$^2$ at a voltage of 6.5 V and a luminescent color was blue (luminous maximum wavelength: 459 nm). In addition, when the device was driven at a constant current with initial emission luminance set to 2000 cd/m$^2$, a time period required for the luminance to reduce by 50% was 1000 hours. When the device was stored at 85° C. for 500 hours, no change in driving voltage was observed.

Examples 7 to 9

In each of the examples, an organic EL device was produced in the same manner as in Example 1 except that a material described in Table 2 was used instead of Compound (12) as a dopant.

Each of the resultant devices was evaluated in the same manner as in Example 6. As a result, as shown in Table 2, blue light emission was observed in each of all the devices. In addition, emission luminance was 500 to 950 cd/m$^2$, and a time period required for the luminance to reduce by 50% was 100 to 200 hours. When each of those devices was stored at 85° C. for 500 hours, no change in driving voltage was observed.

Comparative Example 2

In example 1, an organic EL device was produced in the same manner as in Example 6 except that 1,6-bis(diphenylamino)pyrene was used instead of Compound (12) as a material for a light-emitting layer.

The resultant device was evaluated in the same manner as in Example 6. As a result, as shown in Table 2, blue light emission (luminous maximum wavelength: 465 nm) was observed. In addition, emission luminance was 800 cd/m$^2$, and a time period required for the luminance to reduce by 50% was as short as 600 hours. When the device was stored at 85° C. for 500 hours, no change in driving voltage was observed.

As can be seen from the foregoing, the use of the aromatic amine derivative of the present invention as a dopant for a light-emitting layer significantly improves a half life.

TABLE 2

| | Dopant | Driving voltage (V) | Luminous wavelength (nm) | Emission luminance (cd/m$^2$) | Time period required for luminance to reduce by 50% (hours) | Change in voltage after storage at 85° C. (for 500 hours) |
|---|---|---|---|---|---|---|
| Example 6 | (12) | 6.5 | 459 | 500 | 1000 | No change |
| Example 7 | (15) | 6.5 | 465 | 650 | 1200 | No change |
| Example 8 | (19) | 6.5 | 470 | 800 | 1500 | No change |
| Example 9 | (22) | 6.5 | 477 | 950 | 2000 | No change |

TABLE 2-continued

| | Dopant | Driving voltage (V) | Luminous wavelength (nm) | Emission luminance (cd/m$^2$) | Time period required for luminance to reduce by 50% (hours) | Change in voltage after storage at 85° C. (for 500 hours) |
|---|---|---|---|---|---|---|
| Comparative Example 2 | 1,6-bis(diphenylamino) pyrene | 6.5 | 465 | 800 | 600 | No change |

INDUSTRIAL APPLICABILITY

As described above in detail, each of the aromatic amine derivative of the present invention and the organic EL device using the derivative has high emission luminance, high heat resistance, excellent high-temperature storage stability, and a long lifetime. Therefore, each of them can be highly practically used in, for example, an on-vehicle device, and is useful.

The invention claimed is:

1. An organic electroluminescence device comprising:
a cathode;
an anode; and
one or multiple organic thin film layers including at least a light-emitting layer, the one or multiple organic thin film layers being interposed between the cathode and the anode,
wherein the light-emitting layer comprises:
an anthracene derivative; and
an aromatic amine derivative represented by the following general formula (1):

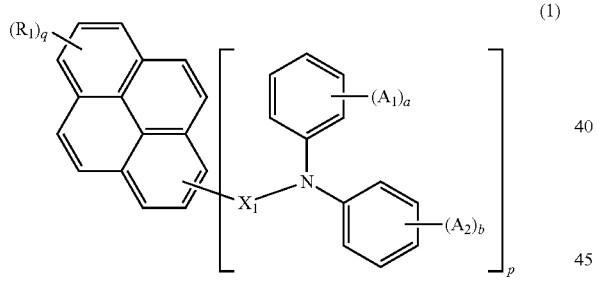

(1)

where:
$A_1$, $A_2$, and $R_1$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 6 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted heterocyclic group having 5 to 50 carbon atoms, or a halogen atom, and $A_1$ and $A_2$ may bind to each other to form a saturated or unsaturated ring provided that chrysene is excluded when $A_1$ and $A_2$ form a saturated or unsaturated ring;
a and b each represent an integer of 0 to 5, and multiple $A_1$s and multiple $A_2$s may be identical to or different from each other, and may bind to each other to form a saturated or unsaturated ring when a and b each represent 2 or more;
p represents an integer of 2, and groups in ( ) may be identical to or different from each other, provided that the groups in ( ) are substituted at the 1- and 6- positions of the pyrene core;
q represents an integer of 0 to 9, and multiple $R_1$s may be identical to or different from each other when q represents 2 or more; and
$X_1$ represents a substituted or unsubstituted arylene group having 5 to 50 carbon atoms.

2. The organic electroluminescence device according to claim 1, wherein the aromatic amine derivative is represented by the following general formula (2):

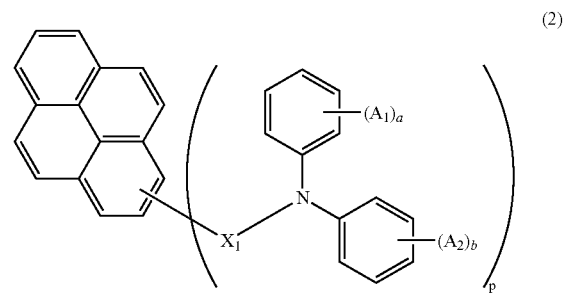

(2)

where:
$A_1$ and $A_2$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 6 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted heterocyclic group having 5 to 50 carbon atoms, or a halogen atom, and $A_1$ and $A_2$ may bind to each other to form a saturated or unsaturated ring provided that chrysene is excluded when $A_1$ and $A_2$ form a saturated or unsaturated ring;
a and b each represent an integer of 0 to 5, and multiple $A_1$s and multiple $A_2$s may be identical to or different from each other, and may bind to each other to form a saturated or unsaturated ring when a and b each represent 2 or more;
p represents an integer of 2, and groups in ( ) may be identical to or different from each other, provided that the groups in ( ) are substituted at the 1- and 6- positions of the pyrene core; and $X_1$ represents a substituted or unsubstituted arylene group having 5 to 50 carbon atoms.

3. The organic electroluminescence device according to claim 1, wherein the aromatic amine derivative is represented by the following general formula (3):

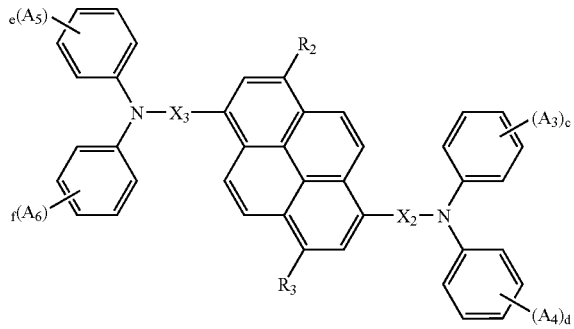

(3)

where:

$A_3$ to $A_6$ and $R_2$ to $R_3$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 6 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted heterocyclic group having 5 to 50 carbon atoms, or a halogen atom, and $A_3$ and $A_4$, and $A_5$ and $A_6$ may bind to each other to form a saturated or unsaturated ring provided that chrysene is excluded when $A_3$ and $A_4$, and $A_5$ and $A_6$ form a saturated or unsaturated ring;

c, d, e, and f each represent an integer of 0 to 5, and multiple $A_3$s, $A_4$s, $A_5$s, and $A_6$s may be identical to or different from each other, and may bind to each other to form a saturated or unsaturated ring when c, d, e, and f each represent 2 or more; and $X_2$ and $X_3$ each independently represent a substituted or unsubstituted arylene group having 5 to 50 carbon atoms.

4. The organic electroluminescence device according to claim 1, wherein the aromatic amine derivative is a doping material.

5. The organic electroluminescence device according to claim 1, wherein the light-emitting layer comprises 0.1-20 wt. % of the aromatic amine derivative.

6. The organic electroluminescence device according to claim 1, wherein at least one of a and b represent an integer of 1 to 5.

7. The organic electroluminescence device according to claim 2, wherein at least one of a and b represent an integer of 1 to 5.

8. The organic electroluminescence device according to claim 3, wherein at least one of c and d represent an integer of 1 to 5, at least one of e and f represent an integer of 1 to 5.

9. The organic electroluminescence device according to claim 1, wherein the light-emitting layer comprises: 10-(4-(naphthylen-1-yl)phenyl)-9-(naphthylen-2-yl)anthracene; and N,N'-(pyrene-1,6-diylbis(4,1-phenylene))bis(N-phenyl-[1,1'-biphenyl]-4-amine).

10. The organic electroluminescence device according to claim 1, wherein the light-emitting layer comprises: 10-(4-(naphthylen-1-yl)phenyl)-9-(naphthylen-2-yl)anthracene; and N,N'-((3,8-diisopropylpyrene-1,6-diyl)bis(4,1-phenylene))bis(N-(3,4-dimethylphenyl)-3,4-dimethylaniline).

11. The organic electroluminescence device according to claim 1, wherein the light-emitting layer comprises: 10-(4-(naphthylen-1-yl)phenyl)-9-(naphthylen-2-yl)anthracene; and 4,4'-(3,8-diphenylpyrene-1,6-diyl)bis(N,N-diphenylaniline).

12. The organic electroluminescence device according to claim 1, wherein the light-emitting layer comprises: 10-(4-(naphthylen-1-yl)phenyl)-9-(naphthylen-2-yl)anthracene; and N,N'-((3,8-diphenylpyrene-1,6-diyl)bis(4,1-phenylene)) bis(N-(3,4-dimethylphenyl)-3,4-dimethylaniline).

13. The organic electroluminescence device according to claim 1, which exhibits a blue luminescent light emission with a half life of 1,000-2,000 hours.

* * * * *